(12) United States Patent
Yoshikawa et al.

(10) Patent No.: US 8,183,256 B2
(45) Date of Patent: May 22, 2012

(54) REMEDY OR PREVENTIVE FOR INTEGRATION DYSFUNCTION SYNDROME

(75) Inventors: Satoru Yoshikawa, Kamakura (JP); Hidenori Mochizuki, Kamakura (JP)

(73) Assignee: Toray Industries, Inc. (JP)

(*) Notice: Subject to any disclaimer, the term of this patent is extended or adjusted under 35 U.S.C. 154(b) by 259 days.

(21) Appl. No.: 12/664,686

(22) PCT Filed: Jun. 20, 2008

(86) PCT No.: PCT/JP2008/061309
§ 371 (c)(1),
(2), (4) Date: Dec. 24, 2009

(87) PCT Pub. No.: WO2009/001764
PCT Pub. Date: Dec. 31, 2008

(65) Prior Publication Data
US 2010/0160364 A1    Jun. 24, 2010

(51) Int. Cl.
*A61K 31/4748* (2006.01)
*A61P 25/18* (2006.01)

(52) U.S. Cl. .......................... 514/282; 546/44
(58) Field of Classification Search ............... 514/282; 546/44
See application file for complete search history.

(56) References Cited

U.S. PATENT DOCUMENTS

| | | | |
|---|---|---|---|
| 5,739,145 A * | 4/1998 | Nagase et al. | 514/282 |
| 5,972,953 A | 10/1999 | Nagase et al. | |
| 6,174,891 B1 | 1/2001 | Nagase et al. | |
| 6,277,859 B1 | 8/2001 | Nagase et al. | |
| 6,323,212 B1 | 11/2001 | Nagase et al. | |
| 6,476,208 B1 * | 11/2002 | Cohen et al. | 536/23.1 |
| 2001/0044449 A1 | 11/2001 | Nagase et al. | |
| 2004/0116456 A1 | 6/2004 | Kumagai et al. | |
| 2006/0069086 A1 * | 3/2006 | Michalow | 514/220 |
| 2007/0191419 A1 | 8/2007 | Takahashi et al. | |
| 2009/0170888 A1 | 7/2009 | Umeuchi et al. | |
| 2009/0275617 A1 | 11/2009 | Ito et al. | |

FOREIGN PATENT DOCUMENTS

| | | |
|---|---|---|
| EP | 0 974 363 A1 | 1/2000 |
| JP | 1-149788 A | 6/1989 |
| JP | 2525552 B2 | 8/1996 |
| JP | 2000-053572 A | 2/2000 |
| JP | 2000-169476 A | 6/2000 |
| JP | 2005-289886 A | 10/2005 |
| WO | 93/15081 A1 | 8/1993 |
| WO | 95/03307 A1 | 2/1995 |
| WO | 98/23290 A1 | 6/1998 |
| WO | 99/05146 A1 | 2/1999 |
| WO | 99/11289 A1 | 3/1999 |
| WO | 01/14383 A1 | 3/2001 |
| WO | 02/078744 A1 | 10/2002 |
| WO | 02/089845 A1 | 11/2002 |
| WO | 2005/085228 A1 | 9/2005 |
| WO | 2006/095836 A1 | 9/2006 |
| WO | 2007/037513 A1 | 4/2007 |
| WO | 2007/100775 A2 | 9/2007 |

OTHER PUBLICATIONS

Zhou et al Effects of phencyclidine on levels of dynorphin-117 and dynorphin 1-8 immunorectivites in various brain regions. Acta Pharmacologica Sinica, 1986 vol. 7, No. 6 pp. 491-495, abstract.*
Margolis, E.B. et al., "κ Opioids Selectively Control Dopaminergic Projecting to the Prefrontal Cortex," *PNAS*, Feb. 21, 2006, vol. 103, No. 8, pp. 2938-2942.
Izenwasser, S. et al., "Characterization of Kappa-Opioid Receptor Binding in Human Insular Cortex," *Life Sciences*, 1999, vol. 65., No. 9, pp. 857-862.

* cited by examiner

*Primary Examiner* — Jennifer M Kim
(74) *Attorney, Agent, or Firm* — DLA Piper LLP (US)

(57) ABSTRACT

A method of treating schizophrenia, which method can treat especially positive symptoms of schizophrenia and does not cause impaired information processing related to cognitive deficiencies or the like which is a symptom of schizophrenia. The method of treating schizophrenia includes as an effective ingredient a compound having a specific morphinan skeleton or a pharmaceutically acceptable acid addition salt thereof.

3 Claims, 1 Drawing Sheet

REMEDY OR PREVENTIVE FOR INTEGRATION DYSFUNCTION SYNDROME

RELATED APPLICATIONS

This is a §371 of International Application No. PCT/JP2008/061309, with an international filing date of Jun. 20, 2008 (WO 2009/001764 A1, published Dec. 31, 2008), which is based on Japanese Patent Application No. 2007-164868, filed Jun. 22, 2007, the subject matter of which is incorporated by reference.

TECHNICAL FIELD

This disclosure relates to a therapeutic or prophylactic agent for schizophrenia, comprising as an effective ingredient a morphinan derivative or a pharmaceutically acceptable acid addition salt thereof.

BACKGROUND

Schizophrenia is a kind of psychiatric diseases which mostly occurs during puberty or adolescence, and its lifetime prevalence is as high as about 1% of the population. Its symptoms are classified into positive symptoms such as psychomotor excitation, hallucinations and delusions; negative symptoms such as loss of spontaneity, apathy and poor rapport; and cognitive deficiencies as discussed in Folia Pharmacol Jpn, 127, 4, 2006.

As a mechanism of pathogenesis of schizophrenia, the hypothesis of excessive dopamine in the brain has been proposed, so that, at present, a typical or atypical antipsychotics whose main pathway is direct blocking of dopamine receptors is used as a therapeutic agent for schizophrenia, which agent is comprehensively applied to the above-described 3 types of symptoms. However, since direct blocking of dopamine receptors may cause side effects such as extrapyramidal symptoms (EPS), a therapeutic agent having a different mode of action and a wide margin of safety is demanded.

As compounds which suppress dopamine release in the brain, opioid κ receptor agonists such as a morphinan compound (WO 99/011289), which is an effective ingredient, nalmefene (Gavin B et al., Neuropsychopharmacology, 30, 2554, 2005) and U-50,488H (Werling L L et al., J. Pharmacol. Exp. Ther., 246, 282, 1988) are known, and, among these, nalmefene, which has a morphinan skeleton in common with the compound, is reported to have actually exerted a therapeutic effect against schizophrenia (Rapaport M H et al., Neuropsychopharmacology, 9, 111, 1993). However, there is a large difference in structures and no suggestion of their having a therapeutic effect against schizophrenia.

Further, on the other hand, U-50,488H which is known to have an inhibitory action on dopamine release has been suggested to have a possibility of causing impaired information processing disorder leading to cognitive deficiencies or the like which is a symptom of schizophrenia (Marco B et al., Biol. Psychiatry, 57, 1550, 2005). However, although the inhibitory action of a specific morphinan compound on dopamine release has been disclosed, there is no suggestion in that publication that a therapeutic effect against schizophrenia is exhibited without causing a side effect such as cognitive deficiencies.

In addition to the above, a morphinan compound is described in WO 93/015081 together with its analgesic activity, diuresis activity, antitussive activity, and agonistic activity to opioid κ receptors.

Further, its uses as a protective agent for brain cells (WO 95/003307), antipruritic (WO 98/023290), therapeutic agent for hyponatremia (WO 99/005146), ORL-1 receptor antagonist (JP 2000-53572 A), therapeutic agent for neuropathic pain (WO 01/014383), therapeutic agent for psychoneurotic disorders (WO 02/078744), therapeutic agent for drug dependence (WO 99/011289), therapeutic agent for sepsis (WO 02/089845), therapeutic agent for pruritus caused by multiple sclerosis (WO 06/095836) and the like have already been disclosed. Among these, although WO 02/078744 discloses a therapeutic use for "psychoneurotic disorders", only an effect against Restless Legs Syndrome (RLS) belonging to a neurological disorder has been disclosed, without disclosing a therapeutic effect against schizophrenia at all.

It could therefore be helpful to provide a therapeutic or prophylactic agent for schizophrenia having a remarkable effect, which therapeutic or prophylactic agent does not cause impaired information processing related to cognitive deficiencies which is a symptom of schizophrenia, and has fewer side effects.

SUMMARY

We discovered that a specific compound having a morphinan skeleton or a pharmaceutically acceptable acid addition salt thereof has a remarkable therapeutic or prophylactic effect against schizophrenia and is useful as a therapeutic or prophylactic agent for especially positive symptoms of schizophrenia, which therapeutic or prophylactic agent does not cause impaired information processing related to cognitive deficiencies, which is a symptom of schizophrenia, and has fewer side effects, thereby completing the disclosure.

We thus provide the following [1] to [5]:

[1] A therapeutic or prophylactic agent for schizophrenia, comprising as an effective ingredient a compound represented by Formula (I) below:

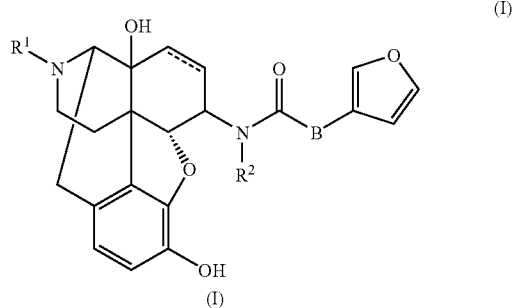

wherein the double line constituted by a dotted line and a solid line represents a double bond or a single bond, $R^1$ represents $C_4$-$C_7$ cycloalkylalkyl, $R^2$ represents $C_1$-$C_5$ linear or branched alkyl, and B represents —CH=CH— or a pharmaceutically acceptable acid addition salt thereof.

[2] The therapeutic or prophylactic agent for schizophrenia according to [1], wherein, in Formula (I), $R^1$ is cyclopropylmethyl, cyclobutylmethyl cyclopentylmethyl or cyclohexylmethyl, and $R^2$ is methyl, ethyl or propyl.

[3] The therapeutic or prophylactic agent for schizophrenia according to [1], wherein the compound represented by Formula (I) is (−)-17-(cyclopropylmethyl)-3,14β-dihydroxy-4,5α-epoxy-6β-[N-methyl-trans-3-(3-furyl)acrylamido]morphinan.

[4] Use of a compound represented by Formula (I):

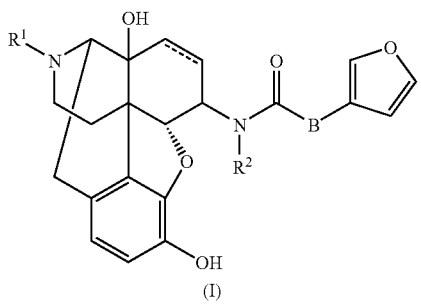

(I)

wherein the double line constituted by a dotted line and a solid line represents a double bond or a single bond, $R^1$ represents $C_4$-$C_7$ cycloalkylalkyl, $R^2$ represents $C_1$-$C_5$ linear or branched alkyl, and B represents —CH=CH— or a pharmaceutically acceptable acid addition salt thereof, for the production of a therapeutic or prophylactic agent for schizophrenia.

[5] A method for therapy or prophylaxis of schizophrenia, the method comprising administration of an effective amount of a compound represented by Formula (I):

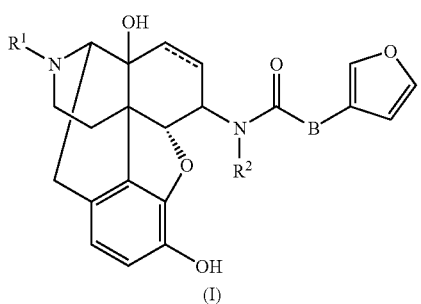

(I)

wherein the double line constituted by a dotted line and a solid line represents a double bond or a single bond, $R^1$ represents $C_4$-$C_7$ cycloalkylalkyl, $R^2$ represents $C_1$-$C_5$ linear or branched alkyl, and B represents —CH=CH— or a pharmaceutically acceptable acid addition salt thereof to a patient in need of therapy or prophylaxis of schizophrenia.

Our compositions and methods have a remarkable therapeutic or prophylactic effect on schizophrenia, and do not cause impaired information processing related to cognitive deficiencies or the like which is a symptom of schizophrenia.

BRIEF DESCRIPTION OF THE DRAWINGS

In FIG. 1, the abscissa indicates the does of the test compounds, and the ordinate indicates the amount of mouse hyperlocomotion (in counts) for 30 minutes (for 30 minutes from 30 minutes after the administration of PCP).

DESCRIPTION OF SYMBOLS

Figure 2:
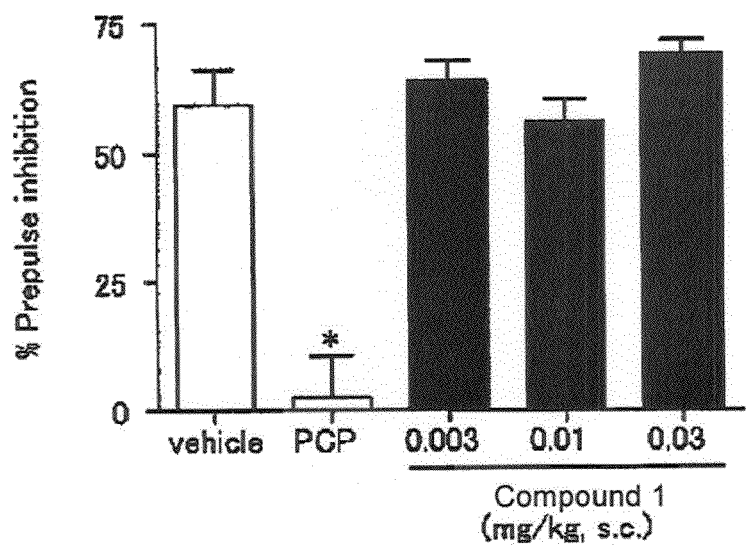

FIG. 2 is a diagram showing an effect of compound 1 on rat PPI in Example 2. In FIG. 2, the abscissa indicates the doses of the test compounds, and the ordinate indicates the inhibition ratio of startle responses % Prepulse Inhibition.

DETAILED DESCRIPTION

The therapeutic or prophylactic agent for schizophrenia comprises as an effective ingredient a compound represented by Formula (1) or a pharmaceutically acceptable acid addition salt thereof:

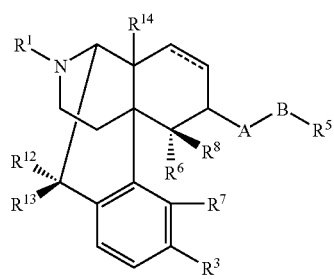

(1)

wherein $R^1$ represents $C_1$-$C_5$ alkyl, $C_4$-$C_7$ cycloalkylalkyl, $C_5$-$C_7$ cycloalkenylalkyl, $C_6$-$C_{12}$ aryl, $C_7$-$C_{13}$ aralkyl, $C_4$-$C_7$ alkenyl, allyl, furan-2-ylalkyl (wherein the number of carbon atoms in the alkyl moiety is 1 to 5), or thiophen-2-ylalkyl (wherein the number of carbon atoms in the alkyl moiety is 1 to 5).

$R^{14}$ represents hydrogen, hydroxy, nitro, $C_1$-$C_5$ alkanoyloxy, $C_1$-$C_5$ alkoxy, $C_1$-$C_5$ alkyl or $NR^9R^{10}$. Here, $R^9$ represents hydrogen or $C_1$-$C_5$ alkyl, $R^{10}$ represents hydrogen, $C_1$-$C_5$ alkyl or —(C=O)$R^{11}$, wherein $R^{11}$ represents hydrogen, phenyl, or $C_1$-$C_5$ alkyl.

$R^3$ represents hydrogen, hydroxy, $C_1$-$C_5$ alkanoyloxy, or $C_1$-$C_5$ alkoxy.

A represents —XC(=Y)—, —XC(=Y)Z—, —X—, or —$XSO_2$— (wherein X, Y and Z each independently represents $NR^4$, S or O, wherein $R^4$ represents hydrogen, $C_1$-$C_5$ linear or branched alkyl, or $C_6$-$C_{12}$ aryl, wherein, in cases where two or more $R^4$ exist, these may be the same with or different from each other).

B represents a valence bond, $C_1$-$C_{14}$ linear or branched alkylene (wherein this may have at least one substituent selected from the group consisting of $C_1$-$C_5$ alkoxy, $C_1$-$C_5$ alkanoyloxy, hydroxy, fluorine, chlorine, bromine, iodine, amino, nitro, cyano, trifluoromethyl, and phenoxy; and 1 to 3 methylene group(s) may be replaced with a carbonyl group(s)), $C_2$-$C_{14}$ linear or branched acyclic unsaturated hydrocarbon having 1 to 3 double bond(s) and/or triple bond(s) (wherein this may have at least one substituent selected from the group consisting of $C_1$-$C_5$ alkoxy, $C_1$-$C_5$ alkanoyloxy, hydroxy, fluorine, chlorine, bromine, iodine, amino, nitro, cyano, trifluoromethyl, and phenoxy; and 1 to 3 methylene group(s) may be replaced with a carbonyl group(s)), or $C_1$-$C_{14}$ linear or branched, saturated or unsaturated hydrocarbon having 1 to 5 thioether bond(s), ether bond(s) and/or amino bond(s) (with the proviso that a hetero atom does not directly bind to A; and 1 to 3 methylene group(s) may be replaced with a carbonyl group(s)).

$R^5$ represents hydrogen or an organic group having any one of the following basic skeletons:

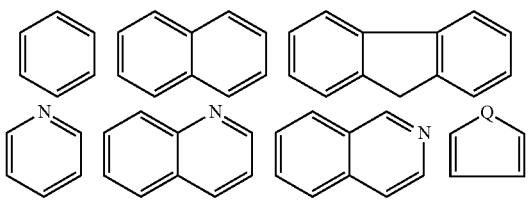

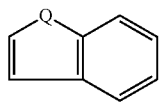  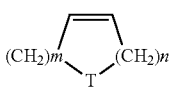

Q: N, O, S
T: $CH_2$, NH, S, O
$l = 0\text{-}5$
$m, n \geq 0$
$m + n \leq 5$

Organic Group Represented by $R^5$ (wherein, in these formulae, Q represents N, O or S; T represents $CH_2$, NH, S or O, l represents an integer of 0 to 5; m and n each independently represents an integer of 0 to 5, the total of m and n being not more than 5; and each of the organic groups may have at least one substituent selected from the group consisting of $C_1\text{-}C_5$ alkyl, $C_1\text{-}C_5$ alkoxy, $C_1\text{-}C_5$ alkanoyloxy, hydroxy, fluorine, chlorine, bromine, iodine, amino, nitro, cyano, isothiocyanato, trifluoromethyl, trifluoromethoxy and methylenedioxy).

$R^6$ represents hydrogen and $R^7$ represents hydrogen, hydroxy, $C_1\text{-}C_5$ alkoxy or $C_1\text{-}C_5$ alkanoyloxy; or $R^6$ and $R^7$ together represent —O—, —$CH_2$—, or —S—.

$R^8$ represents hydrogen, $C_1\text{-}C_5$ alkyl or $C_1\text{-}C_5$ alkanoyl.

$R^{12}$ and $R^{13}$ together represent hydrogen; or one of these represents hydrogen and the other represents hydroxy; or these together represent oxo.

Formula (1) includes (+), (−) and (±) isomers.

The double line in Formula (1) includes a dotted line and a solid line and represents a double bond or a single bond, and is preferably a single bond.

The therapeutic or prophylactic agent for schizophrenia preferably comprises as an effective ingredient, among the compounds represented by Formula (1), a compound represented by the above-described Formula (I) or a pharmaceutically acceptable acid addition salt thereof as a main ingredient. The double line constituted by a dotted line and a solid line in Formula (I) represents a double bond or a single bond, and is preferably a single bond.

In Formula (I), $R^1$ represents $C_4\text{-}C_7$ cycloalkylalkyl. In particular, $R^1$ is preferably cyclopropylmethyl, cyclobutylmethyl, cyclopentylmethyl or cyclohexylmethyl, especially preferably cyclopropylmethyl.

$R^2$ represents $C_1\text{-}C_5$ linear or branched alkyl. $R^2$ is preferably methyl, ethyl or propyl. Among these, methyl is preferred.

B represents —CH=CH—. B is preferably trans form —CH=CH—.

As the compound represented by Formula (I), a compound wherein $R^1$ is cyclopropylmethyl, $R^2$ is methyl and B is trans form —CH=CH—, that is, (+17-(cyclopropylmethyl)-3,14β-dihydroxy-4,5α-epoxy-6β-[N-methyl-trans-3-(3-furyl)acrylamido]morphinan is especially preferred, but the disclosure is not limited thereto.

The compounds represented by the General Formula (I) can be produced according to the method described in JP 2525552 B. Among the compounds represented by the General Formula (1), ones wherein both $R^{12}$ and $R^{13}$ are hydrogen can be produced according to the method described in JP 2525552 B. Among the compounds represented by the General Formula (1), a compound wherein $R^{12}$ and $R^{13}$ together represent oxo can be produced, for example, according to the method described in Chem. Pharm. Bull., 52, 664 (2004) and JP 2525552 B, using as a raw material a compound having 10-oxo, which can be obtained according to a literature (Heterocycle, 63, 865 (2004), Bioorg. Med. Chem. Lett., 5, 1505 (1995)). Further, among the compounds represented by the General Formula (1), a compound wherein $R^{12}$ is hydroxy and $R^{13}$ is hydrogen can be produced according to the method described in Chem. Pharm. Bull., 52, 664 (2004).

Examples of the pharmaceutically acceptable acid addition salt include inorganic acid salts such as hydrochloric acid salt, sulfuric acid salt, nitric acid salt, hydrobromic acid salt, hydroiodic acid salt and phosphoric acid salt; organic carboxylic acid salts such as acetic acid salt, lactic acid salt, citric acid salt, oxalic acid salt, glutaric acid salt, malic acid salt, tartaric acid salt, fumaric acid salt, mandelic acid salt, maleic acid salt, benzoic acid salt and phthalic acid salt; and organic sulfonic acid salts such as methanesulfonic acid salt, ethanesulfonic acid salt, benzenesulfonic acid salt, p-toluenesulfonic acid salt and camphorsulfonic acid salt. Among these, hydrochloric acid salt, hydrobromic acid salt, phosphoric acid salt, tartaric acid salt, methanesulfonic acid salt and the like are preferably used, but, needless to say, the pharmaceutically acceptable acid addition salt is not limited thereto.

The compound represented by Formula (I) or a pharmaceutically acceptable acid addition salt thereof is purified such that it can be applied to medical use, and can then be orally administered as it is or as a pharmaceutical composition after mixing with a known pharmaceutically acceptable acid, carrier, vehicle and/or the like. The formulation for the oral administration can be selected from the group consisting of tablets, capsules, powders, granules and the like, but is not limited thereto.

The content of the compound represented by Formula (I) or a pharmaceutically acceptable acid addition salt thereof in the pharmaceutical composition is not limited, and can be normally prepared such that a dose of 0.1 μg to 100 mg per administration is attained. The dose can be appropriately selected depending on the symptom, age and body weight of the patient, the method of administration, and the like, and is normally 0.1 μg to 20 mg, preferably about 1 μg to 10 mg per day per adult in terms of the amount of the compound represented by Formula (I), which dose can be attained by one or several times of administration.

When administering the therapeutic or prophylactic agent for schizophrenia, the compound or a pharmaceutically acceptable salt thereof can be administered solely or in combination with one or more kinds of drugs used for therapy or prophylaxis of a disease, or for alleviation or inhibition of symptoms. When the therapeutic or prophylactic agent for schizophrenia is administered in combination with one or more other drugs, the therapeutic or prophylactic agent and the drug(s) may be separately administered or may be administered after being mixed together. Examples of such a drug include typical antipsychotics such as chlorpromazine, fluphenazine, haloperidol, loxapine, mesoridazine, molindone, perphenazine, pimozide, thioridazine, thiothixene and trifluoperazine; and atypical antipsychotic agents such as aripiprazole, clozapine, olanzapine, quetiapine, risperidone and ziprasidone, although these are merely examples and should not be interpreted as limiting the drug.

The term "schizophrenia" includes all of the (1) positive symptoms, (2) negative symptoms, (3) cognitive deficiencies, and the like. Among these, the therapeutic or prophylactic agent for schizophrenia can be especially preferably used for therapy or prophylaxis of positive symptoms.

The above-described compound or a pharmaceutically acceptable acid addition salt thereof, which is an effective ingredient of the therapeutic or prophylactic agent of the present invention, can be confirmed to be effective for therapy and/or prophylaxis of schizophrenia according to the method described in Jpn. J. Pharmacol., 66, 181, 1994. The hyperlocomotion of an animal induced by Phencyclidine (PCP) which is used in this method is known as a phenotype of positive symptoms of schizophrenia in human. Further, PCP is known to be capable of causing induction of not only positive symptoms but also negative symptoms and cognitive deficiencies of schizophrenia in human and animals (Javitt D C et al., *Am. J. Psychiatry*, 148, 1301, 1991, Volkow N D et al., *Semin. Nucl. Med.*, 22, 254, 1992), and the fact that the present compound shows effectiveness in this model induced by PCP indicates that it is effective against schizophrenia.

Further, the fact that there is no risk, in the above-described compound or a pharmaceutically acceptable acid addition salt thereof, of causing impaired information processing related to cognitive deficiencies which is a symptom of schizophrenia can be confirmed by investigating the effect of the compound on the phenomenon wherein the startle response to a startle stimulus (pulse) in an animal is inhibited by presentation of a weak stimulus (prepulse) prior to presentation of a startle stimulus (pulse) (Prepulse Inhibition, PPI) according to the method described in Bio. Psychiatry., 57, 1550, 2005. In this method, inhibition of PPI indicates abnormality in information processing, and is known to reflect cognitive deficiencies, which is a symptom of schizophrenia, and the like.

EXAMPLES

Our compositions and methods will now be described concretely by way of Examples.

Example 1

Effect of (−)-17-(Cyclopropylmethyl)-3,14β-Dihydroxy-4,5α-Epoxy-6β-[N-Methyl-Trans-3-(3-Furyl) Acrylamido]Morphinan Hydrochloric Acid Salt (Compound 1) on Mouse PCP-induced Hyperlocomotion In the experiments, 12 to 14 ddy male mice of 7 to 8 weeks old per each group were used. Each mouse was placed in a measuring cage (22 cm×38 cm×20 cm: W×L×H) arranged under an infrared counter, and habituated thereto for 2 hours until the start of measurement. Subsequently, phencyclidine (PCP, 10 mg/kg) was subcutaneously administered to the mouse, which was then returned to the measuring cage, and the locomotor activity of the mouse was measured by Supermex (Muromachi Kikai Co., Ltd) every 5 minutes. The measurement time was 90 minutes. Treatment with the test compound was carried out by subcutaneous administration of the compound dissolved in a vehicle, 1 minute before the administration of PCP.

The structure of the compound 1 can be represented by Formula (II) below:

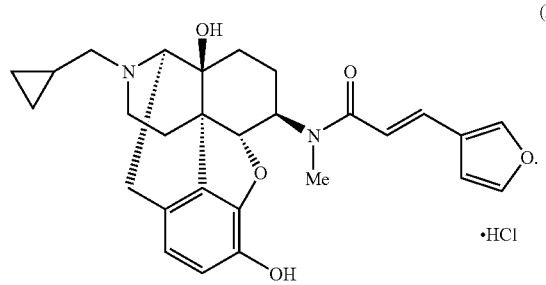

(II)

Figure 1:
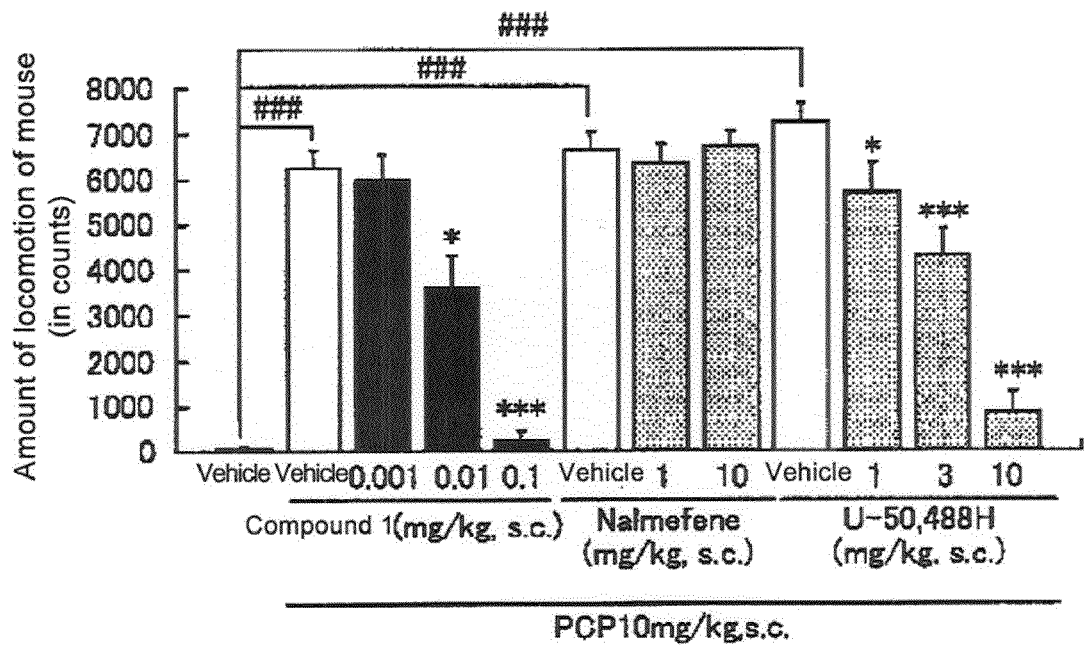
FIG. 1 is a diagram showing effects of compound 1, nalmefene and U-50,488H on mouse PCP-induced hyperlocomotion in Example 1.

The result is shown in FIG. 1. The PCP-induced hyperlocomotion known as a model of positive symptoms of schizophrenia was statistically significantly inhibited by 0.01 mg/kg or more of the compound 1 ($p<0.05$ and $p<0.001$, respectively, against the vehicle-administered group). This indicates that the compound 1 has a remarkable therapeutic effect against schizophrenia.

In FIG. 1, "*" and "***" represent less than 5% and less than 0.1%, respectively, of significance levels, indicating the statistical significance. This also applies to FIG. 2.

Reference Example 1

In the same manner as in Example 1, Nalmefene and U-50,488H were evaluated. The results are shown in FIG. 1. Nalmefene did not have any effect on the amount of locomotion even by the treatment at a dose of 10 mg/kg. U-50,488H showed a significant inhibitory effect, although treatment with a dose as high as 1 mg/kg was required ($p<0.05$ and $p<0.001$, respectively, against the vehicle-administered group). Thus, compared to nalmefene and U-50,488, the compound 1 was confirmed to have a more remarkable effect.

Example 2

Effect of Compound 1 on Startle Response in Rat Prepulse Inhibition (PPI) Model

In the experiments, 8 SD male rats of 9 to 10 weeks old were used per each group. The measurement was carried out using an apparatus for measuring startle responses of small animals (San Diego Instruments). Each rat was placed in a special folder (having a diameter of about 8 cm, manufactured by Plexiglas), and habituated to the measuring environment for 10 minutes, followed by measurement of the startle response under the conditions of: 80 dB prepulse, 120 dB pulse and the prepulse-pulse interval of 100 msec, to calculate % Prepulse Inhibition [((pulse reaction without prepulse−pulse reaction after prepulse)/(pulse reaction without prepulse)×100]. Treatment with the test compound was carried out by subcutaneous administration of the compound dissolved in a vehicle, 30 minutes before beginning of the stimulation session.

The result is shown in FIG. 2. In the PPI model, the compound 1 did not inhibit PPI even under the treatment at a dose of 0.03 mg/kg (s.c.). As a positive control in the evaluation system, Phencyclidine (PCP: 4 mg/kg), which has been reported to inhibit PPI, was used, and a statistically significant inhibitory effect on PPI was observed ($p<0.05$ against the vehicle-administered group).

From the above results, it was proved that the compound 1 does not cause impaired information processing related to cognitive deficiencies which is a symptom of schizophrenia, which disorder has been reported for U-50,488H.

INDUSTRIAL APPLICABILITY

We provide a therapeutic or prophylactic agent with high safety for schizophrenia, which therapeutic or prophylactic agent has an excellent therapeutic effect against schizophrenia and does not cause impaired information processing related to cognitive deficiencies which is a symptom of schizophrenia.

The invention claimed is:

1. A method of treating schizophrenia comprising administering an effective amount of a compound represented by Formula (I) below:

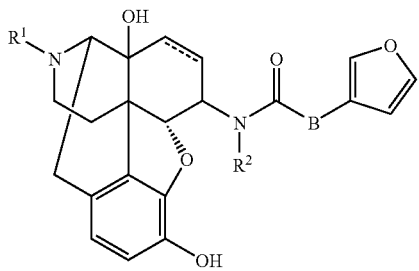

(I)

wherein the double line is a dotted line and a solid line and represents a double bond or a single bond, $R^1$ represents $C_4$-$C_7$ cycloalkylalkyl, $R^2$ represents $C_1$-$C_5$ linear or branched alkyl, and B represents —CH=CH— or a pharmaceutically acceptable acid addition salt thereof to a patient in need thereof.

2. The method according to claim 1, wherein $R^1$ is cyclopropylmethyl, cyclobutylmethyl, cyclopentylmethyl or cyclohexylmethyl and $R^2$ is methyl, ethyl or propyl.

3. The method according to claim 1, wherein the compound is (−)-17-(cyclopropylmethyl)-3, 14β-dihydroxy-4,5α-epoxy-6β-[N-methyl-trans-3-(3-furyl)acrylamido]morphinan.

* * * * *

UNITED STATES PATENT AND TRADEMARK OFFICE
CERTIFICATE OF CORRECTION

PATENT NO.        : 8,183,256 B2
APPLICATION NO.   : 12/664686
DATED             : May 22, 2012
INVENTOR(S)       : Yoshikawa et al.

It is certified that error appears in the above-identified patent and that said Letters Patent is hereby corrected as shown below:

<u>On the Title Page, item [30]</u>

Insert Foreign Application -- Japan 2007 – 164868 06/22/2007 --

<u>In Column 5,</u>

Line 54, change "(+17" to -- (-)-17 --

Signed and Sealed this
Twenty-third Day of October, 2012

David J. Kappos
*Director of the United States Patent and Trademark Office*